Aug. 23, 1966 G. J. VON ABRAMS Plant Pat. 2,664
ROSE PLANT
Filed Feb. 12, 1965
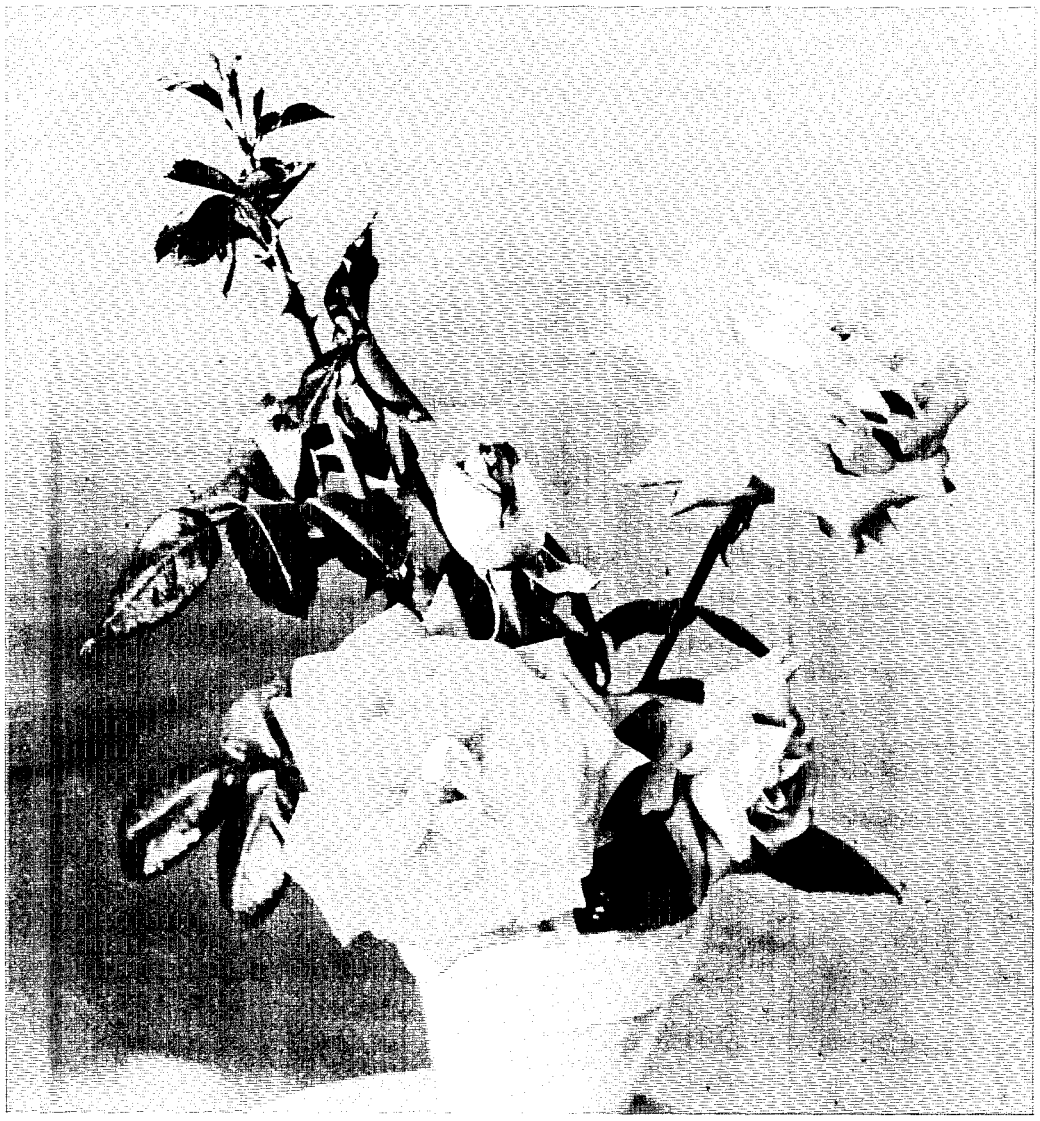

United States Patent Office

Plant Pat. 2,664
Patented August 23, 1966

2,664
ROSE PLANT

Gordon J. Von Abrams, 614 Laurel Place, Davis, Calif.

Filed Feb. 12, 1965, Ser. No. 432,437
1 Claim. (Cl. Plt.—12)

The invention relates to a new and distinct variety of rose plant of the hybrid tea class, originated by me in June 1955 as a consequence of a breeding program begun in 1949. The parentage of my new rose plants is as follows:

Multnomah × (Pinocchio × Saturnia), the seed parent × Carrousel × (L. E. Longley × Charles Mallerin), the pollen parent.

The object of the cross was the production of a fragrant, bicolored rose of high color contrast, with a bloom of classical form borne on a vigorous, disease resistant plant. These objectives were achieved along with other desirable improvements, as evidenced by the following unique combination of characteristics which are outstanding in the new variety and which distinguish it from its parents as well as from all other varieties of which I am aware. My new variety is primarily characterized by:

An intense, distinct fragrance of fresh, ripe, red raspberries; an unusually sharp contrast between the colors of the deeply pigmented blood red upper and chalk white lower surfaces of the petals; an unusually effective display of this contrast brought about by the production of solitary, large, sculptured flowers of classical form in which the whorls of petals reflex in reduced degree and with reduced speed centripetally and in which the petal margins curl slightly downward, hiding the lightly pigmented marginal band on the reverse of the petals, which events together result in the rich red of the upper surface of the petal being displayed in regular tiered order against what appears to the eye to be the chalk white reverse of the petal; large, abundant, very glossy foliage which is unusually heavily red pigmented when young and which remains pigmented and of the color of purple-leaved forms of Prunus for an unusually long time.

Asexual reproduction of my new variety by budding, through a series of annual propagations at Scappoose, Oregon and Livermore, California shows that all characteristics of the variety come true to form through succeeding propagations. The accompanying photographs illustrate the primary characteristics of my new variety as nearly true as is reasonably possible to make them with presently available techniques. The color references cited are those of the Horticultural Colour Charts of the Royal Horticultural Society.

The following botanical description is based upon observation of greenhouse grown plants produced under average conditions at Livermore, California, November 1964 and on garden specimens in the All America Rose Trial Gardens during 1961–1962.

Plant upright, almost fastigiate, regularly producing canes from the base. Axillary growth and basal shoots erect, never spreading. Stems strong and stout, rather heavily pigmented when young, medium green when mature, becoming striated and tan when old, bearing numerous stout thorns proximally, thorns becoming more scattered distally and under conditions of rapid growth; thorns of several sizes ranging from small ones interspersed between the larger, 3 mm. long by ½ mm. tall, to extremely large stout thorns at the base of strong canes, about 13 mm. long by 14 mm. tall and 5 mm. across. Most thorns less than twice as long as tall at the base except the smaller ones which may be twice as long as tall (e.g. 6 mm. long x 3 mm. tall). Thorns somewhat hooked, gibbous, reddish-green when young, tan to brown when old, points very sharp and hard, tip of the thorns descending well below the mid line of the base.

Foliage large, glossy, with five leaflets except for the three or four leaves immediately below the flowers which are generally tripartite, sometimes simple; when simple with one or two lobes. Leaf rachis grooved above, armed below, light green below, reddish-green along the groove; thorns of the rachis scattered, not conspicuously associated with the petiolules. Leaflets broadly ovate to slightly obovate. Terminal leaflet about 50–75 mm. long by 35–45 mm. broad, veining not especially conspicuous above, midvein very prominent below, secondary veins slightly raised near the midrib, lateral pinnae similar but smaller, about 45–60 mm. long by 30–37 mm. broad. The margins of the leaflets doubly serrate, somewhat crisp, giving the leaf a slightly cupped shape, concave from below. The larger serrations about 1½ mm. long by 1½ mm. at the base, the smaller barely more than a stout trichome. The color of the foliage Fern Green (HCC 0862/2) heavily overlain Oxblood Red (HCC 00823), heavily pigmented when young resembling purple leafed plums in color, when mature, dark Sage Green (HCC 000861) above, medium Sage Green (HCC 00861/1) below, the lower surface often with persistent light cyanin pigmentation of Oxblood Red (HCC 00823/3).

The number of internodes below the flower, 7–14. The fifth internode below the flower of a 12 noded stem 30–35 mm. long under November greenhouse conditions at Livermore, California.

Ordinarily only one axillary bud is activated when a flower is removed.

The flowers are borne singly, but the 2 or 3 nodes immediately below the flower are only weakly vegetative.

The peduncle is stout, 4–5 mm. in diameter, 95–100 mm. long, strong, supporting the large flowers well and remaining erect when the flowers are cut. The peduncle is armed with numerous prickles up to 3 mm. long, reddish in color, very thin and sharp. The receptacle is slightly urceolate, about 8 mm. long by 9 mm. across at the middle. The sepals are five, 50 mm. or more with alternate margins foliaceous, ornate, with numerous lobes. The sepals reflex completely before the petals reflex. The flowers are large, well formed, double and intensely fragrant. The fragrance is fruity with delicate nuances of cedar resulting in a total odor reminiscent of ripe red raspberries. The petals are large, cuneate, about 50 mm. broad and 55 mm. long, white on the reverse, dark red on the upper surface, with some tinting on the reverse with Tyrian Purple (HCC 727/2), especially at the margins of the petals. Upper surface Blood Red (HCC 820) overlain Purple Madder (HCC 1028). Base of the petals Dresden Yellow (HCC 64/2 to 64/1) with a clearly delineated "eye" on the upper surface ¼" deep by ½" across; fully open bloom Cherry Red (HCC 722) overlain Currant Red (HCC 821). The guard petals are imperfect and show considerable anthocyanin pigmentation, Tyrian Purple (HCC 727/2), on the reverse. The petals range in number from about 15 to 22, with more or less, depending on ambient temperatures at the time petal primordia are initiated. Petaloidia 8–13 in number, sometimes more or less, extremely varied in size; 5–45 mm. broad by 8–55 mm. long varying in degree of perfection, ranging from nearly perfect large petaloidia to barely petalaceous staminodia which occur in about equal numbers. The inner staminodia are much crinkled and distorted. Stamens numerous, fused at the base or free, 7–10 mm. long, about 45–60 in number. The anthers are yellow, 2½ mm. long by 1½ mm. wide, producing little pollen.

Disc prominent, elevated 1½ mm. above the calyx, 2 mm. across, smooth in aspect, but lightly grooved radially, creamy to white.

The pistils ordinary, normal, about 10–15 mm. long, variable in length depending on placement of the ovary on the hypanthium wall. Stigmas capitate, small, about ½ mm. in diameter, lobed, translucent, cream to light yellow. Styles slender, about 8–13 mm. long, Cardinal Red (HCC 822) distally, white to greenish proximally, pubescent over much of their length, densely so below, sparsely, or not at all, below the stigma. The pubescence, hyaline, silky, up to 2 mm. in length. The ovaries normal about 2 mm. long and 1 mm. wide. No fruit has been observed.

Having thus disclosed my invention, I claim:

A new and distinct variety of rose plant of the hybrid tea class substantially as herein shown and described, primarily characterized by: an intense, distinct fragrance of fresh, ripe, red raspberries; an unusually sharp contrast between the colors of the deeply pigmented blood red upper and chalk white lower surfaces of the petals; an unusually effective display of this contrast brought about by the production of solitary, large, sculptured flowers of classical form in which the whorls of petals reflex in reduced degree and with reduced speed centripetally and in which the petal margins curl slightly downward, hiding the lightly pigmented marginal band on the reverse of the petals, which events together result in the rich red of the upper surface of the petal being displayed in regular tiered order against what appears to the eye to be the chalk white reverse of the petal; large, abundant, very glossy foliage which is unusually heavily red pigmented when young and which remains pigmented and of the color of purple leaved forms of Prunus for an unusually long time.

No references cited.

ANTONIO F. GUIDA, *Acting Primary Examiner.*

R. E. BAGWILL, *Assistant Examiner.*